US010624616B2

United States Patent
Mukherjee et al.

(10) Patent No.: US 10,624,616 B2
(45) Date of Patent: Apr. 21, 2020

(54) SURGICAL INSTRUMENTS INCLUDING SENSORS

(71) Applicant: Covidien LP, Mansfield, MA (US)

(72) Inventors: Nilay Mukherjee, Acton, MA (US); Andrew Miesse, Durham, CT (US); David C. Racenet, Killingworth, CT (US)

(73) Assignee: Covidien LP, Mansfield, MA (US)

( * ) Notice: Subject to any disclaimer, the term of this patent is extended or adjusted under 35 U.S.C. 154(b) by 380 days.

(21) Appl. No.: 15/370,145

(22) Filed: Dec. 6, 2016

(65) Prior Publication Data

US 2017/0172550 A1 Jun. 22, 2017

Related U.S. Application Data

(60) Provisional application No. 62/269,223, filed on Dec. 18, 2015.

(51) Int. Cl.
  *A61B 17/00* (2006.01)
  *A61B 5/00* (2006.01)
  (Continued)

(52) U.S. Cl.
  CPC ............ *A61B 17/00* (2013.01); *A61B 5/0084* (2013.01); *A61B 5/022* (2013.01); *A61B 5/0261* (2013.01); *A61B 5/1072* (2013.01); *A61B 5/4836* (2013.01); *A61B 5/6843* (2013.01); *A61B 5/6847* (2013.01); *A61B 17/068* (2013.01); *A61B 17/29* (2013.01); *A01N 1/0247* (2013.01); *A61B 5/1076* (2013.01); *A61B 5/1459* (2013.01); *A61B 2017/00022* (2013.01); *A61B 2017/00026* (2013.01); *A61B 2017/00057* (2013.01); *A61B 2017/00106* (2013.01); *A61B 2017/00115* (2013.01); *A61B 2017/00199* (2013.01); *A61B 2017/2926* (2013.01);
  (Continued)

(58) Field of Classification Search
  CPC combination set(s) only.
  See application file for complete search history.

(56) References Cited

U.S. PATENT DOCUMENTS 4,109,647 A 8/1978 Stern et al.
4,862,894 A 9/1989 Fujii
(Continued)

FOREIGN PATENT DOCUMENTS

WO   03/101277 A2   12/2003
WO   2007008057 A1   1/2007

OTHER PUBLICATIONS

European Search Report dated May 4, 2017, corresponding to European Application No. 16204749.2; 10 total pages.
(Continued)

*Primary Examiner* — Sean P Dougherty
(74) *Attorney, Agent, or Firm* — Carter, DeLuca & Farrell LLP (57) ABSTRACT

A surgical instrument includes a handle portion, first and second jaw members operably coupled to the handle portion, and first and second sensors associated with the first or second jaw members. The first sensor is configured to measure local perfusion in tissue grasped between the first and second jaw members, and the second sensor is configured to measure a pressure applied to the tissue by the first and second jaw members.

14 Claims, 4 Drawing Sheets

(51) Int. Cl.
*A61B 5/022* (2006.01)
*A61B 5/026* (2006.01)
*A61B 5/107* (2006.01)
*A61B 17/068* (2006.01)
*A61B 17/29* (2006.01)
*A01N 1/02* (2006.01)
*A61B 5/1459* (2006.01)
*A61B 90/00* (2016.01)

(52) U.S. Cl.
CPC ..... *A61B 2090/065* (2016.02); *A61B 2505/05* (2013.01); *A61B 2562/063* (2013.01)

(56) References Cited

U.S. PATENT DOCUMENTS

| | | | |
|---|---|---|---|
| 5,395,033 A | 3/1995 | Byrne et al. | |
| 5,518,164 A | 5/1996 | Hooven | |
| 5,722,419 A | 3/1998 | Semmlow et al. | |
| 5,769,791 A | 6/1998 | Benaron et al. | |
| 7,223,279 B2 | 5/2007 | Burbank et al. | |
| 7,229,465 B2 | 6/2007 | Burbank et al. | |
| 7,618,376 B2 | 11/2009 | Kimball | |
| 8,002,795 B2 | 8/2011 | Beetel | |
| 8,073,518 B2 | 12/2011 | Chin | |
| 8,118,206 B2 | 2/2012 | Zand et al. | |
| 8,157,145 B2 | 4/2012 | Shelton, IV et al. | |
| 8,303,622 B2* | 11/2012 | Alkhatib ............ | A61B 17/0401 600/117 |
| 8,808,311 B2 | 8/2014 | Heinrich et al. | |
| 9,204,830 B2 | 12/2015 | Zand et al. | |
| 2003/0120306 A1 | 6/2003 | Burbank et al. | |
| 2003/0236452 A1* | 12/2003 | Melker ............... | A61B 5/0873 600/323 |
| 2004/0087987 A1* | 5/2004 | Rosenberg ............ | A61B 17/12 606/157 |
| 2004/0127800 A1 | 7/2004 | Kimball et al. | |
| 2005/0131390 A1 | 6/2005 | Heinrich et al. | |
| 2005/0256522 A1* | 11/2005 | Francischelli ..... | A61B 18/1442 606/41 |
| 2006/0020167 A1* | 1/2006 | Sitzmann ........... | A61B 1/00039 600/173 |
| 2006/0235314 A1 | 10/2006 | Migliuolo et al. | |
| 2006/0273135 A1* | 12/2006 | Beetel ................. | A61B 17/068 227/175.1 |
| 2007/0203505 A1 | 8/2007 | Burbank et al. | |
| 2009/0054908 A1 | 2/2009 | Zand et al. | |
| 2009/0192360 A1* | 7/2009 | Riess .................... | A61B 17/02 600/210 |
| 2011/0144640 A1 | 6/2011 | Heinrich et al. | |
| 2011/0306840 A1* | 12/2011 | Allen ................. | A61B 1/00158 600/202 |
| 2012/0116415 A1* | 5/2012 | Forsell ................... | A61B 17/29 606/119 |
| 2013/0110088 A1* | 5/2013 | Wenchell ......... | A61B 17/07207 606/1 |
| 2014/0107697 A1 | 4/2014 | Patani et al. | |
| 2014/0135604 A1 | 5/2014 | Cuesta Valentin et al. | |
| 2014/0288386 A1 | 9/2014 | Zand et al. | |
| 2015/0148827 A1* | 5/2015 | Otten ................... | A61B 17/083 606/157 |
| 2015/0224326 A1* | 8/2015 | Toth ...................... | A61B 5/042 600/301 |
| 2016/0206336 A1* | 7/2016 | Frushour .......... | A61B 17/07207 |
| 2017/0143891 A1* | 5/2017 | Bridges .............. | A61M 1/3638 |
| 2018/0242861 A1* | 8/2018 | Inoue ..................... | A61B 5/026 |

OTHER PUBLICATIONS

European Communication dated Oct. 22, 2018 corresponding to European Application No. 16 204 749.2; 5 pages.

* cited by examiner

SURGICAL INSTRUMENTS INCLUDING SENSORS

CROSS-REFERENCE TO RELATED APPLICATIONS

The present application claims priority to, and the benefit of, U.S. Provisional Patent Application Ser. No. 62/269,223, filed on Dec. 18, 2015, the entire contents of which are hereby incorporated by reference.

BACKGROUND

1. Technical Field

The present disclosure relates to surgical instruments and, more particularly, to surgical graspers for grasping tissue and for determining characteristics of the grasped tissue in preparation for performing various surgical procedures.

2. Background of Related Art

Colorectal surgery sometimes requires anastomosis, which involves resecting a piece of diseased bowel tissue and creating a new connection between presumably two healthy bowel segments. Typically, before performing the anastomosis, the amount of tissue to be resected is estimated using visual indicia of the bowel. The goal is to preserve as much healthy tissue as possible while at the same time removing all of the diseased tissue.

A risk involved in performing an anastomotic procedure is anastomotic leaks, which can be a serious complication that can result in an acute life-threatening condition. The anastomotic leaks are typically caused by a failure to resect all of the diseased tissue. Current methods used in estimating the amount of tissue to be resected during an anastomotic procedure are sometimes inadequate in preventing all anastomotic leaks.

Accordingly, a need exists for surgical instruments that can sense, either sequentially or simultaneously, a multitude of parameters and factors of the bowel tissue to aid a surgeon in performing a more successful anastomotic surgical procedure.

SUMMARY

In one aspect of the present disclosure, a surgical instrument is provided and includes a handle portion, first and second jaw members, and first and second sensors. The jaw members are operably coupled to the handle portion and movable relative to one another in response to an actuation of the handle portion. The first sensor is associated with the first or second jaw member and is configured to measure local perfusion in tissue grasped between the first and second jaw members. The second sensor is associated with the first or second jaw member and configured to measure a pressure applied to the tissue by the first and second jaw members.

In some embodiments, each of the first and second jaw members may include a tissue contacting surface. The first and second sensors may be disposed on the tissue contacting surface of the first or second jaw member.

In some embodiments, the surgical instrument may include third and fourth sensors. The third sensor may be configured to measure the local perfusion in the tissue grasped between the first and second jaw members, and the fourth sensor may be configured to measure the pressure applied to the tissue by the first and second jaw members. The first and second sensors may be disposed on the tissue contacting surface of the first jaw member, and the third and fourth sensors may be disposed on the tissue contacting surface of the second jaw member.

In some embodiments, the first and third sensors may overlap with one another and the second and fourth sensors may overlap with one another when the first and second jaw members are in an approximated position.

In some embodiments, the tissue contacting surface of the first and/or second jaw member may define a plurality of teeth configured for atraumatically grasping tissue.

In some embodiments, the first and second sensors may be arranged in a linear array along a longitudinal axis defined by the first jaw member.

In some embodiments, the surgical instrument may further include a display disposed on the handle portion and in communication with the first and second sensors. The display may be configured to display the measured local perfusion and the measured pressure applied to the tissue by the first and second jaw members. The display may include three discreet display sections disposed in a linear array along a longitudinal axis defined by the handle portion. The display may have an elongated configuration and extend along a longitudinal axis defined by the handle portion. The display may be configured to display an index representative of the ratio of a surface perfusion pressure measured using the first and second sensors and a systemic blood pressure.

In some embodiments, the first sensor may be a Doppler flow sensor configured to measure the local perfusion in the tissue using Laser-Doppler flowmetry, light scattering, and/or light absorption.

In some embodiments, the surgical instrument may further include a third sensor associated with the first or second jaw member. The third sensor is configured to measure a thickness of the tissue grasped between the first and second jaw members. The first jaw member may include a tissue contacting surface having each of the first, second, and third sensors disposed thereon. The third sensor may be a slide potentiometer, a rotational potentiometer, or a linear variable differential transformer.

In some embodiments, the surgical instrument may be pre-programmed to clamp tissue at a predetermined clamping pressure known to cease perfusion through the tissue.

In another aspect of the present disclosure, a method of performing a surgical procedure is provided. The method includes positioning tissue between first and second jaw members of a surgical instrument, determining local perfusion of the tissue using a first sensor associated with the first or second jaw member, determining a pressure applied to the tissue by the first and second jaw members using a second sensor associated with the first or second jaw member, determining a surface perfusion pressure of the tissue using the determined local perfusion and the determined pressure applied to the tissue, and determining, using the measured surface perfusion pressure of the tissue, whether the tissue is viable.

Some methods may further include displaying the determined local perfusion and the determined pressure applied to the tissue on a display of the surgical instrument.

Some methods may further include displaying on the display an index representative of the ratio of the surface perfusion pressure and a systemic blood pressure.

Some methods may further include clamping the tissue between the first and second jaw members at a predetermined clamping pressure known to cease perfusion through the tissue, reducing the clamping pressure at a predetermined rate, and sending the determined pressure to the display at the moment when perfusion through the tissue restarts.

Some methods may further include determining a thickness of the tissue using a third sensor associated with one of the first or second jaw members, and determining, using the measured thickness of the tissue, a size of staples to be used in stapling the tissue.

These and other objects will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Embodiments of the presently disclosed surgical instruments and systems will now be described in detail with reference to the drawing figures wherein like reference numerals identify similar or identical elements. As used herein and as is traditional, the term "distal" will refer to that portion which is further from the user while the term "proximal" will refer to that portion which is closer to the user.

Figure 1A:
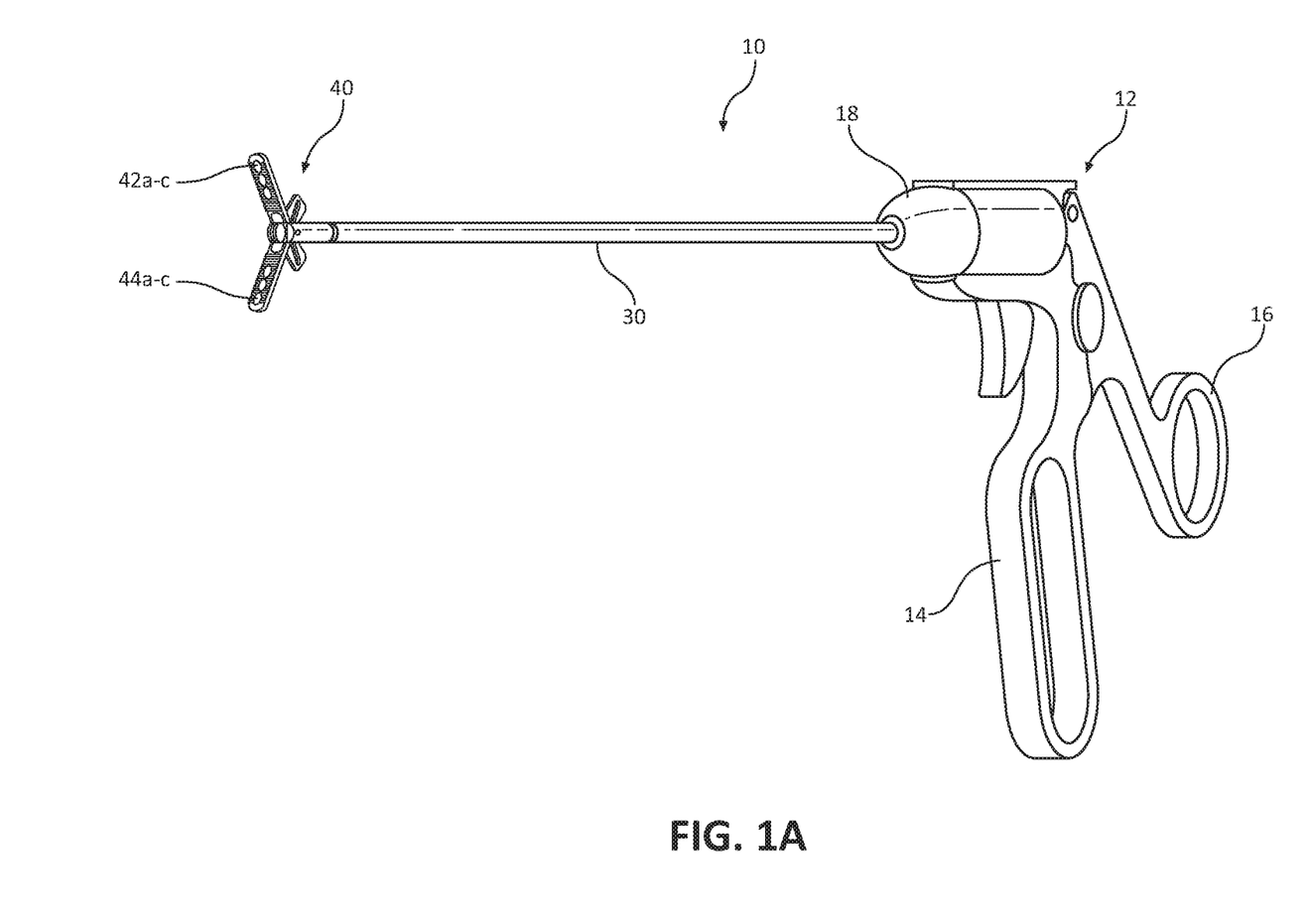
FIG. 1A is a front, perspective view of a surgical instrument including sensors and a display, in accordance with the present disclosure.
Figure 1B:
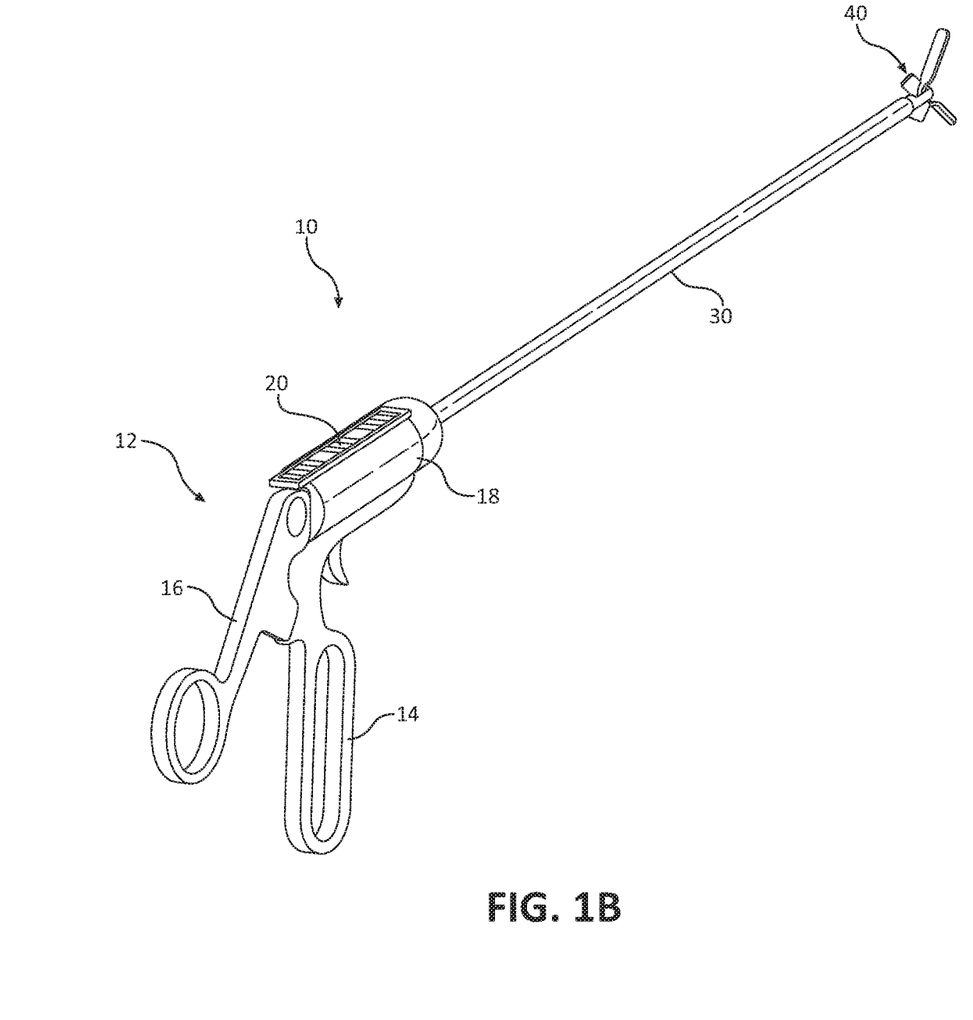
FIG. 1B is a rear, perspective view of the surgical instrument of FIG. 1A.

With reference to FIGS. 1A and 1B, a surgical instrument, such as, for example, a tissue grasper 10 is provided. The tissue grasper 10 is configured to grasp tissue and sense a multiplicity of biological parameters of the grasped tissue to assist a surgeon in performing a surgical procedure, for example, an anastomotic surgical procedure, as will be described in detail herein. The tissue grasper 10 generally includes a handle portion 12, an elongated shaft 30, and a jaw assembly 40.

The handle portion 12 of the tissue grasper 10 includes a stationary handle 14 and a pivoting or movable handle 16 pivotably coupled to the stationary handle 14. Manipulation of the pivoting handle 16 relative to the stationary handle 14 effects a closing of the jaw assembly 40 to grasp tissue. The handle portion 12 of the tissue grasper 10 includes a longitudinal body portion 18 formed with the stationary handle 14. The body portion 18 has a display 20, for example, an LED display or liquid-crystal display ("LCD") for displaying various tissue parameters measured by various sensors 42a-c, 44a-c of the tissue grasper 10.

Figure 2:
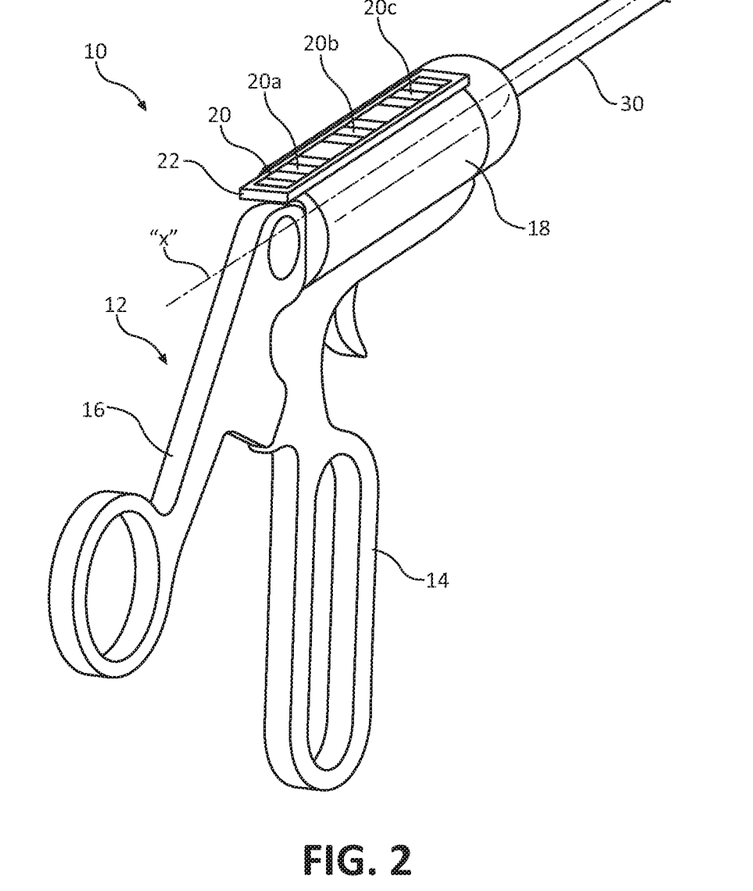
FIG. 2 is an enlarged view of a handle portion of the surgical instrument of FIG. 1A illustrating the display of the surgical instrument.
Figure 3:
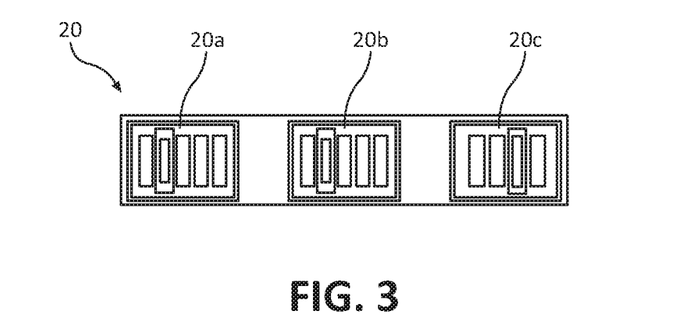
FIG. 3 is an enlarged view of the display of FIG. 2.

With reference to FIGS. 2 and 3, the body portion 18 of the handle portion 12 defines a longitudinal axis "X" that is coaxial with a longitudinal axis defined by the elongated shaft 30. The body portion 18 has a planar upper surface 22 on which the display 20 is situated. It is contemplated that the display 20 may be disposed at any suitable location of the body portion 18 or on any other component of the tissue grasper 10.

The display 20 may have multiple display sections, for example, three display sections 20a, 20b, 20c, arranged in a linear array along the longitudinal axis "X." It is contemplated that the display 20 may include more or less than three discrete display sections. A first display section 20a of the display 20 is configured to display a visual indication of a measured tissue perfusion of tissue grasped by the tissue grasper 10. A second display section 20b of the display 20 is configured to display a visual indication of a measured amount of pressure being applied to tissue grasped by the tissue grasper 10. A third display section 20c of the display 20 is configured to display a measured thickness of the tissue grasped by the tissue grasper 10.

The visual indication displayed by each of the display sections 20a, 20b, 20c includes a range of colors increasing in brightness from a proximal portion to a distal portion thereof. For example, when viewing each of the first and second display sections 20a, 20b in a proximal to distal direction, the first and second display sections 20a, 20b may each be green, yellow, orange, and then red, with each color portion gradually blending into the adjacent color portion. Other colors and color arrangements for the first and second display sections 20a, 20b are contemplated. The tissue grasper 10 may be configured such that when the green of the first display section 20a is lit, this may indicate a relatively high tissue perfusion being measured by the tissue grasper 10, whereas when the red of the first display section 20a is lit, this may indicate a relatively low tissue perfusion being measured by the tissue grasper 10. The information related to the tissue perfusion may be useful when making a determination on the viability of the tissue being grasped, as will be described in more detail below.

With reference to the second display section 20b of the display 20, when the green of the second display section 20b is lit, this may be indicative of a relatively low grasping or clamping pressure being applied to tissue by the tissue grasper 10, whereas when the red of the second display section 20b is lit, this may be indicative of a relatively high grasping or clamping pressure being applied to tissue by the tissue grasper 10. The clamping pressure measured by the tissue grasper 10 and displayed by the second display section 20b of the tissue grasper 10 is used in conjunction with the tissue perfusion displayed by the first display section 20a of the tissue grasper 10 to determine the perfusion pressure of the grasped tissue.

The perfusion pressure is measured by applying a sufficient amount of clamping pressure on the subject tissue until there is no perfusion (i.e., no blood flow) through the tissue, and then slowly reducing the clamping pressure until perfusion through the grasped tissue restarts. The pressure at which the perfusion restarts is the tissue perfusion pressure. For a detailed description of a method of measuring surface perfusion pressure, reference may be made to U.S. Pat. No. 7,618,376, the entire contents of which are incorporated by reference herein.

The information related to the amount of pressure being applied to tissue by the tissue grasper 10 may also be useful in preventing over-compression of tissue to prevent damage to healthy tissue.

In viewing the third display section 20c from a proximal to distal direction, the third display section 20c may be grey, brown, violet, and black. In some embodiments, third display section 20c may be grey, white, blue, purple, tan, green, and black. Other colors and color arrangements for the third display section 20c are contemplated. When the grey (proximal portion) of the third display section 20c is lit, this may be an indication that tissue grasped by the tissue grasper 10 has a relatively small thickness (i.e., the tissue is too thin to withstand being stapled), whereas when the black (distal portion) of the third display section 20c is lit, this may be an indication that tissue grasped by the tissue grasper 10 has a relatively large thickness (i.e., the tissue is too thick to be stapled). The information related to tissue thickness may be useful for making a determination on the size of the staples to be used when performing a surgical anastomosis on the grasped tissue.

In some embodiments, instead of display 20 utilizing ranges of colors or brightness to illustrate the measured tissue parameters (e.g., tissue perfusion, tissue compression, and tissue thickness), the display 20 may display ranges of numbers or various numeral outputs. In particular, the first, second, and third display sections 20a, 20b, 20c may display the number ranges 0 to 3, 0 to 5, 0 to 10, 0 to 100, or any other suitable range, to illustrate information about the tissue being grasped by the tissue grasper 10. For example, when the first display section 20a displays the number 0, this may be an indication that the grasped tissue has very little or no perfusion (i.e., no blood flow), whereas when the first display section 20a displays the number 100, this may be an indication that the grasped tissue has a high perfusion (i.e., ideal blood flow).

In some embodiments, the display 20 may illustrate information about grasped tissue utilizing any suitable indicia, for example, words such as poor, satisfactory, or good.

In some embodiments, tissue grasper 10 may not include display 20, and instead, tissue grasper 10 may be configured to be connected to or be in communication with another type of display, for example, a tablet, a cell phone, a computer monitor, a laptop, or any suitable display device. Tissue grasper 10 may be connected to any of the aforementioned display devices via USB wires, Wi-Fi, or the like.

Figure 4:
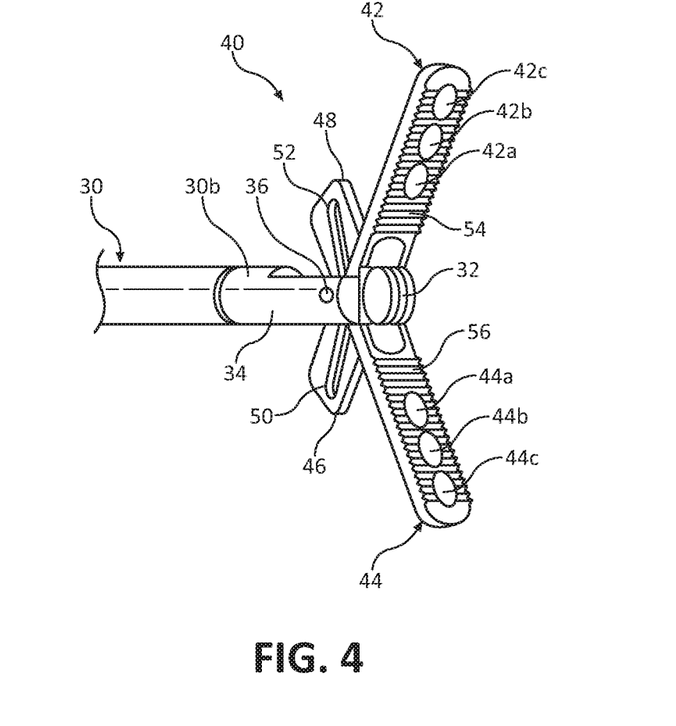
FIG. 4 is an enlarged view of a jaw assembly of the surgical instrument of FIG. 1A illustrating sensors incorporated therein.

With reference to FIGS. 1A, 1B, and 4, the elongated shaft 30 of tissue grasper 10 extends distally from the handle portion 12 and houses an actuation rod (not explicitly shown). The elongated shaft 30 may be rotatable with respect to the handle portion 12 to rotate the jaw assembly 40 about the longitudinal axis "X." The elongated shaft 30 has two prongs 32, 34 formed at its distal end 30b. A pivot pin 36 extends transversely through the prongs 32, 34 and the jaw assembly 40 to provide a point about which the jaw members 42, 44 of the jaw assembly 40 pivot. The actuation rod has a proximal end (not shown) operably coupled to the movable trigger 16 (FIGS. 1A, 1B), and a distal end (not shown) extending between the prongs 32, 34 and which is operably coupled to the jaw assembly 40.

Figure 5:
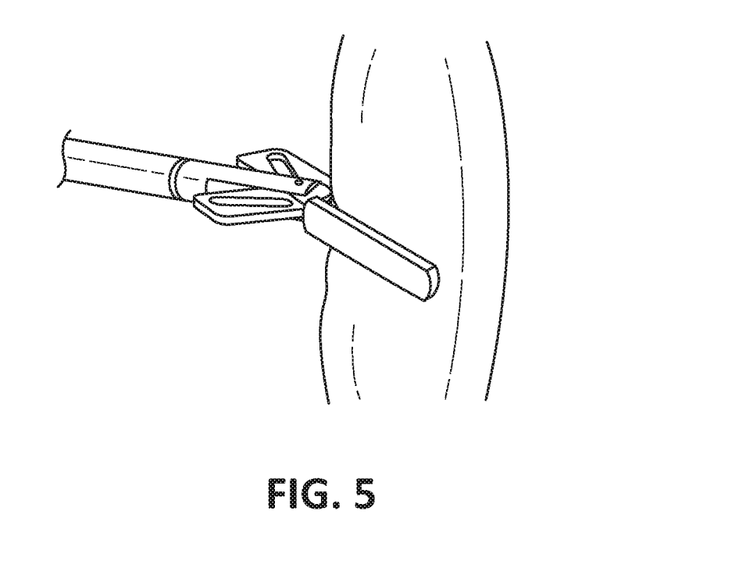
FIG. 5 is a top view of the surgical instrument of FIG. 1A illustrating the jaw assembly grasping tissue.

With reference to FIGS. 4 and 5, the jaw assembly 40 includes first and second juxtaposed jaw members 42, 44, respectively, which are simultaneously movable between a substantially approximated position, in which the jaw members 42, 44 are in relatively close relation to one another, and a spaced position, in which the jaw members 42, 44 are separated at least a sufficient distance to receive tissue therebetween, for example, tissue "T." The jaw assembly 40 includes a first proximal portion or a first flange 46 extending proximally from the first jaw member 42, and a second proximal portion or a second flange 48 extending proximally from the second jaw member 44. The flanges 46, 48 each include an elongated angled cam slot 50, 52 defined therethrough configured to engage the distal end of the actuation rod (not explicitly shown) that drives the opening and closing of the jaw members 42, 44 as the actuation rod moves through the cam slots 50, 52. As such, manipulation of the pivoting handle 16 (FIGS. 1A, 1B) relative to the stationary handle 14 actuates the actuation rod to effect an opening or a closing of the jaw assembly 40 about tissue "T."

With continued reference to FIGS. 4 and 5, the jaw members 42, 44 each have a tissue contacting surface 54, 56 such that when the jaw assembly 40 is in the closed configuration, tissue "T" is grasped between the tissue contacting surfaces 54, 56. The jaw members 42, 44 each have a first sensor 42a, 44a, a second sensor 42b, 44b, and a third sensor 42c, 44c, disposed on respective tissue contacting surfaces 54, 56. The sensors 42a-c, 44a-c are arranged on respective tissue contacting surfaces 54, 56 in a linear array along a longitudinal axis defined by respective jaw members 42, 44. In some embodiments, the sensors 42a-c, 44a-c may be arranged on respective tissue contacting surfaces 54, 56 in any suitable manner.

The first sensors 42a, 44a of the jaw assembly 40 are perfusion sensors, for example, Doppler flow sensors, configured to measure local perfusion (i.e., blood flow) through tissue grasped between the jaw members 42, 44. The first sensors 42a, 44a may measure perfusion of the grasped tissue on the basis of known techniques, such as Laser-Doppler Flowmetry ("LDF"), measuring light scattering, and/or measuring absorption of light from one or more LED's or other light sources. For a detailed description of LDF technology, reference may be made to U.S. Pat. Nos. 4,109,647 and 4,862,894, the entire contents of each of which are incorporated by reference herein.

In some embodiments, only one of the tissue contacting surfaces 54, 56 of the jaw assembly 40 has a perfusion sensor. The first sensors 42a, 44a are in communication, via lead wires or wireless connection, with the first display section 20a of the display 20 such that upon the first sensors 42a, 44a measuring the perfusion in grasped tissue, the first sensors 42a, 44a transmit the measurement data to the first display section 20a, which displays the measurement in any of the manners described above with reference to FIGS. 2 and 3 (e.g., a range of colors, brightness levels, numbers, words.)

In some embodiments, the first sensors 42a, 44a may also be in communication, via lead wires or wireless connection, with a computing device or processor (not shown) such as a laser Doppler monitor, which processes the information collected by the first sensors 42a, 44a to calculate the tissue perfusion. The computing device may also be in communication, via lead wires or wireless connection, with the first display section 20a to send the processed information related to the tissue perfusion to the first display section 20a so that the first display section 20a can display the tissue perfusion in any of the manners described above with reference to FIGS. 2 and 3 (e.g., colors, brightness levels, numbers, words.)

With continued reference to FIGS. 4 and 5, the second sensors 42b, 44b of the jaw assembly 40 are pressure sensors or pressure measuring devices, for example, MEMS devices. For a detailed description of various MEMS devices, reference may be made to U.S. Pat. No. 8,808,311, the entire contents of which are incorporated by reference herein. The second sensors 42b, 44b are configured to measure the amount of pressure applied by the tissue grasper 10 to the grasped tissue (i.e., the clamping pressure). In some embodiments, only one of the tissue contacting surfaces 54, 56 has a pressure sensor. The second sensors 42b, 44b are in electrical communication, via lead wires of wireless connection, with the second display section 20b of the display 20 such that upon the second sensors 42b, 44b measuring the clamping pressure applied to the grasped tissue, the second sensors 42b, 44b transmit the measurement data to the second display section 20b, which displays the measurement in any of the manners described above with reference to FIGS. 2 and 3 (e.g., colors, brightness levels, numbers, words.) Additionally or alternately, the second sensors 42b, 44b may send the measured clamping pressure to the computing device for processing, which then sends the information to the display 20.

The third sensors 42c, 44c of the jaw assembly 40 are gap determination elements, for example, slide potentiometers, rotational potentiometers, devices used to measure impedance between the contacting surfaces 54, 56, or Linear Variable Differential Transformers ("LVDT"), configured to measure the thickness of the grasped tissue by measuring the gap distance between the jaw members 42, 44. For a detailed description of various sensors capable of measuring tissue thickness, reference may be made to U.S. Pat. No. 8,002,795, the entire contents of which are incorporated by reference herein. In some embodiments, only one of the tissue contacting surfaces 54, 56 has a gap determination element. The third sensors 42c, 44c are in electrical communication, via wire leads or wireless connection, with the third display section 20c of the display 20 such that upon the third sensors 42c, 44c measuring the tissue thickness of the grasped tissue, the third sensors 42c, 44c transmit the measurement data to the third display section 20c, which displays the measurement in any of the manners described above with reference to FIGS. 2 and 3 (e.g., colors, brightness levels, numbers, words.) Additionally or alternately, the third sensors 42c, 44c may be in communication, via lead wires or wireless connection, to the computing device, which receives the tissue thickness measurements from the third sensors 42c, 44c, and processes the measurement data and then sends the information to the display 20.

In some embodiments, the display 20 may include a fourth display section (not shown) configured to display an index representative of the ratio of the surface perfusion pressure measured by first sensors 42a, 44a and second sensors 42b, 44b of the tissue grasper 10, and a systemic blood pressure measured by a blood pressure cuff (not shown), as will be described in detail below.

In operation, the tissue grasper 10 may be used prior to, during, or after a surgical procedure, for example, an anastomotic surgical procedure, to gather various data about the subject tissue. In an anastomotic surgical procedure, unhealthy or diseased bowel tissue is resected and the ends of the remaining healthy segments of bowel are stapled together to recreate a continuous bowel. Prior to stapling the ends of the separate bowel segments to one another, the viability of the ends of the separate bowel segments should be assessed in order to predict the likelihood of post-surgery anastomotic leaks or other adverse outcomes. To aid in making this viability assessment, a surgeon may make use of the tissue grasper 10 of the present disclosure.

In use of the tissue grasper 10, each of the two ends of the presumably healthy bowel segments are grasped, either separately or together, between the tissue contacting surfaces 54, 56 of the jaw assembly 40. While monitoring the perfusion reading (i.e., blood flow) displayed on the first display section 20a of the tissue grasper 10, the pivoting handle 16 is manipulated to gradually increase the clamping pressure until the perfusion reading indicates that no blood flow or virtually no blood flow is moving through the grasped tissue. While continuously monitoring both the first and second display sections 20a, 20b, the movable handle 16 of the tissue grasper 10 is manipulated to gradually reduce the amount of clamping pressure being applied to the tissue. The clamping pressure is reduced until first display section 20a displays a perfusion reading indicating that blood flow has returned to the grasped tissue. At the moment that the perfusion reading indicates that the blood flow is returned, the clamping pressure reading displayed by the second display section 20b is noted, which is the local perfusion pressure of the grasped tissue. The measured local perfusion pressure may be used to assess the viability of the grasped tissue. Additionally or alternately, the measured local perfusion pressure may be used in combination with other measurements, for example, a systemic blood pressure reading, to aid in making the determination of the viability of the tissue.

The systemic blood pressure may be taken using any suitable device, for example, a blood pressure cuff, applied to any suitable body portion of the patient, for example, the arm of the patient. An index may be calculated by taking a ratio of the local perfusion pressure measured by the tissue grasper 10 and the systemic blood pressure taken using the blood pressure cuff. The index may be calculated by the computing device and displayed as a number on the display 20 of the tissue grasper 10. The calculated index is predictive of whether an anastomotic leak may occur and/or the grade of an anastomotic leak. As such, a surgeon can use the index to make a determination on whether the two ends of the presumed healthy bowel segments are healthy enough to be stapled together and whether more tissue needs to be resected. For a detailed description of a method of calculating a perfusion index, reference may be made to U.S. Pat. No. 7,618,376, the entire contents of which were incorporated by reference above.

In some embodiments, the tissue grasper 10 may be pre-programmed to clamp tissue at a predetermined clamping pressure that is known to result in perfusion through the grasped tissue to stop. The tissue grasper 10 may also be pre-programmed to reduce the clamping pressure at a predetermined rate and automatically send the pressure reading to the computing device at the moment when perfusion through the grasped tissue restarts. The perfusion pressure reading may also be displayed on the display 20. This automated process eliminates human error in operating the tissue grasper 10 by controlling the amount of clamping pressure being applied to the tissue instead of the surgeon.

The tissue grasper 10 may also be used to determine the size of the staples to be used in stapling the bowel segments together. The staple size may be determined by viewing the third display section 20c of the tissue grasper 10, which indicates the thickness of the grasped tissue. The leg height of the staples selected for the stapling procedure will correspond to the thickness of the tissue. It is contemplated that the tissue thickness measured by the third sensors 42c, 44c may be sent to the computing device, which has stored therein a look-up table that contains a staple size corresponding to each tissue thickness measurement.

In addition to the tissue grasper 10 being used to ensure that the tissue is in condition for stapling or acceptable for stapling, the tissue grasper 10 may also be used as a check after the staples have been fired to ensure that the tissue is healthy (e.g., has good blood flow, is healing properly, etc).

The tissue grasper 10 may also be configured to be incorporated into a robotic surgical system (not shown). The robotic surgical system is powered locally or remotely, and has electronic control systems localized in a console or distributed within or throughout the robotic surgical system. The robotic surgical system permits a surgeon to remotely manipulate the tissue grasper to more precisely control the movement of the tissue grasper 10. The tissue grasper 10 may be configured to send the measurements gathered by the sensors 42a-c, 44a-c to an interface of the robotic surgical system on which the measurements may be displayed for the surgeon to read.

Although the illustrative embodiments of the present disclosure have been described herein, it is understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed is:

1. A surgical instrument, comprising:
   a handle portion;
   first and second jaw members operably coupled to the handle portion and movable relative to one another in response to an actuation of the handle portion;
   a first sensor associated with one of the first or second jaw members and configured to measure local perfusion in tissue grasped between the first and second jaw members;
   a second sensor associated with one of the first or second jaw members and configured to measure a pressure applied to the tissue by the first and second jaw members;
   a display disposed on the handle portion; and
   a processor in communication with the first and second sensors, wherein the processor is configured to display on the display:
   the measured local perfusion;
   the measured pressure applied to the tissue by the first and second jaw members; and
   an index representative of the ratio of a surface perfusion pressure measured using the first and second sensors and a systemic blood pressure, wherein the processor is pre-programmed to:
   apply a clamping pressure to the tissue by the first and second jaw members sufficient to cease perfusion through the tissue;
   reduce the clamping pressure applied to the tissue by the first and second jaw members after the perfusion through the tissue ceases; and
   automatically send the pressure measured by the second sensor to the display when the first sensor determines that perfusion through the grasped tissue restarts.

2. The surgical instrument according to claim 1, wherein each of the first and second jaw members includes a tissue contacting surface, the first and second sensors being disposed on the tissue contacting surface of one of the first or second jaw members.

3. The surgical instrument according to claim 2, further comprising:
   a third sensor configured to measure the local perfusion in the tissue grasped between the first and second jaw members; and
   a fourth sensor configured to measure the pressure applied to the tissue by the first and second jaw members, wherein the first and second sensors are disposed on the tissue contacting surface of the first jaw member, and the third and fourth sensors are disposed on the tissue contacting surface of the second jaw member.

4. The surgical instrument according to claim 3, wherein the first and third sensors overlap with one another and the second and fourth sensors overlap with one another when the first and second jaw members are in an approximated position.

5. The surgical instrument according to claim 2, wherein the tissue contacting surface of at least one of the first or second jaw members defines a plurality of teeth configured for atraumatically grasping tissue.

6. The surgical instrument according to claim 1, wherein the first and second sensors are coaxial with a central longitudinal axis defined by the first jaw member.

7. The surgical instrument according to claim 1, wherein the display includes three discreet display sections disposed in a linear array along a longitudinal axis defined by the handle portion.

8. The surgical instrument according to claim 1, wherein the display has an elongated configuration and extends along a longitudinal axis defined by the handle portion.

9. The surgical instrument according to claim 1, wherein the first sensor is a Doppler flow sensor configured to measure the local perfusion in the tissue using at least one of Laser-Doppler flowmetry, light scattering, or light absorption.

10. The surgical instrument according to claim 1, further comprising a third sensor associated with one of the first or second jaw members and configured to measure a thickness of the tissue grasped between the first and second jaw members.

11. The surgical instrument according to claim 10, wherein the first jaw member includes a tissue contacting surface, each of the first, second, and third sensors disposed on the tissue contacting surface.

12. The surgical instrument according to claim 10, wherein the third sensor is selected from the group consisting of a slide potentiometer, a rotational potentiometer, and a linear variable differential transformer.

13. A tissue grasper, comprising:
    a handle portion;
    an elongated shaft extending distally from the handle portion;
    first and second jaw members operably coupled to the handle portion and movable relative to one another in response to an actuation of the handle portion;
    a first sensor disposed on one of the first or second jaw members and configured to measure local perfusion in tissue grasped between the first and second jaw members;
    a second sensor disposed on one of the first or second jaw members and configured to measure a pressure applied to the tissue by the first and second jaw members;
    a display disposed on the handle portion; and
    a processor in communication with the first and second sensors, wherein the processor is configured to display on the display:
    the measured local perfusion;
    the measured pressure applied to the tissue by the first and second jaw members; and
    an index representative of the ratio of a surface perfusion pressure measured using the first and second sensors and a systemic blood pressure, wherein the processor is pre-programmed to:
    apply a clamping pressure to the tissue by the first and second jaw members sufficient to cease perfusion through the tissue;
    reduce the clamping pressure applied to the tissue by the first and second jaw members after the perfusion through the tissue ceases; and automatically send the pressure measured by the second sensor to the display when the first sensor determines that perfusion through the grasped tissue restarts.

14. A surgical instrument, comprising:
a handle portion;
first and second jaw members operably coupled to the handle portion and movable relative to one another in response to an actuation of the handle portion;
a first sensor associated with one of the first or second jaw members and configured to measure local perfusion in tissue grasped between the first and second jaw members;
a second sensor associated with one of the first or second jaw members and configured to measure a pressure applied to the tissue by the first and second jaw members; and
a processor configured to:
  cause the first and second jaw members to clamp the tissue therebetween to cease perfusion through the tissue;
  reduce a clamping pressure of the first and second jaw members after perfusion through the tissue ceases; and
  send the pressure measured by the second sensor to a display when the first sensor determines that perfusion through the grasped tissue restarts.

* * * * *